US012268780B1

(12) United States Patent
Morrison

(10) Patent No.: US 12,268,780 B1
(45) Date of Patent: *Apr. 8, 2025

(54) TRANSPARENT WATER NANOLIPID FLUID (DNLF) DISPERSIONS AND METHOD OF PREPARATION USING A TWIN SCREW EXTRUDER

(71) Applicant: Eric Morrison, West Saint Paul, MN (US)

(72) Inventor: Eric Morrison, West Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/497,819

(22) Filed: Oct. 8, 2021

Related U.S. Application Data

(60) Provisional application No. 63/089,342, filed on Oct. 8, 2020.

(51) Int. Cl.
| | |
|---|---|
| A61K 9/107 | (2006.01) |
| A61K 9/51 | (2006.01) |
| A61K 31/01 | (2006.01) |
| A61K 31/015 | (2006.01) |
| A61K 31/05 | (2006.01) |
| A61K 31/122 | (2006.01) |
| A61K 31/167 | (2006.01) |
| A61K 31/192 | (2006.01) |
| A61K 31/216 | (2006.01) |
| A61K 31/245 | (2006.01) |
| A61K 31/355 | (2006.01) |
| A61K 31/375 | (2006.01) |
| A61K 31/593 | (2006.01) |
| A61K 31/616 | (2006.01) |
| A61K 36/185 | (2006.01) |
| A61K 36/23 | (2006.01) |
| A61K 36/28 | (2006.01) |
| A61K 36/45 | (2006.01) |
| A61K 36/54 | (2006.01) |
| A61K 36/73 | (2006.01) |
| A61K 36/752 | (2006.01) |
| B01F 23/41 | (2022.01) |
| B01F 27/42 | (2022.01) |
| B01F 101/22 | (2022.01) |

(52) U.S. Cl.
CPC .......... *A61K 9/1075* (2013.01); *A61K 9/5123* (2013.01); *A61K 9/5192* (2013.01); *A61K 31/01* (2013.01); *A61K 31/015* (2013.01); *A61K 31/05* (2013.01); *A61K 31/122* (2013.01); *A61K 31/167* (2013.01); *A61K 31/192* (2013.01); *A61K 31/216* (2013.01); *A61K 31/245* (2013.01); *A61K 31/355* (2013.01); *A61K 31/375* (2013.01); *A61K 31/593* (2013.01); *A61K 31/616* (2013.01); *A61K 36/185* (2013.01); *A61K 36/23* (2013.01); *A61K 36/28* (2013.01); *A61K 36/45* (2013.01); *A61K 36/54* (2013.01); *A61K 36/73* (2013.01); *A61K 36/752* (2013.01); *B01F 23/4105* (2022.01); *B01F 23/4145* (2022.01); *B01F 27/421* (2022.01); B01F 2101/22 (2022.01); B01F 2215/0431 (2013.01); B01F 2215/0472 (2013.01); B01F 2215/0481 (2013.01)

(58) Field of Classification Search
CPC .. A61K 9/1075; A61K 9/5123; A61K 9/5192; A61K 31/01; A61K 31/015; A61K 31/05; A61K 31/122; A61K 31/167; A61K 31/192; A61K 31/216; A61K 31/245; A61K 31/355; A61K 31/375; A61K 31/593; A61K 31/616; A61K 36/185; A61K 36/23; A61K 36/28; A61K 36/45; A61K 36/54; A61K 36/73; A61K 36/752; B01F 23/4105; B01F 23/4145; B01F 27/421; B01F 2101/22; B01F 2215/0431; B01F 2215/0472; B01F 2215/0481
See application file for complete search history.

(56) References Cited

U.S. PATENT DOCUMENTS

2017/0296496 A1* 10/2017 Morrison ............. A61K 9/0014

OTHER PUBLICATIONS

Heurtault B, Saulnier P, Pech B, Proust JE, Benoit JP. A novel phase inversion-based process for the preparation of lipid nanocarriers. Pharm Res. Jun. 2002;19(6):875-80. doi: 10.1023/a:1016121319668. PMID: 12134960.

Lamprecht A, Saumet J, Roux J, Benoit J. Lipid nanocarriers as drug delivery system for ibuprofen in pain treatment. Int J Pharm . Jul. 8, 2004; 278 ( 2 ): 407-14.

Anton N, Gayet P, Benoit JP, Saulnier P. Nano-emulsions and nanocapsules by the PIT method: an investigation on the role of the temperature cycling on the emulsion phase inversion. Int J Pharm. Nov. 1, 2007;344(1-2):44-52. doi: 10.1016/j.ijpharm.2007.04.027. Epub May 6, 2007. PMID: 17592746.

Abdel-Mottaleb M, Neumann D, Lamprecht A. Lipid nanocapsules for dermal application: a comparative study of lipid—based versus polymer-based nanocarriers . Eur J Pharm Biopharm . Sep. 2011;79( 1): 36-42.

(Continued)

Primary Examiner — Jessica Worsham
(74) Attorney, Agent, or Firm — Merchant & Gould P.C.

(57) ABSTRACT

The present invention provides a method of preparing a lipid nanoparticle dispersion using a twin screw extruder. The inventive DNLF fluids are isotropic fluids which include greater than 25% lipophilic content in the form of lipidic nanoparticles dispersed in a continuous aqueous matrix with turbidity less than 375 nephelometric turbidity units (NTU).

23 Claims, No Drawings

(56) References Cited

OTHER PUBLICATIONS

Hong SS, Kim SH, Lim SJ. Effects of triglycerides on the hydrophobic drug loading capacity of saturated phosphatidylcholine-based liposomes. Int J Pharm. Apr. 10, 2015;483(1-2):142-50. doi: 10.1016/j.ijpharm.2015.02.013.
Dragicevic-Curic N, Scheglmann D, Albrecht V, Fahr A. Temoporfin-loaded invasomes: development, characterization and in vitro skin penetration studies. J Control Release. Apr. 7, 2008;127(1):59-69. doi: 10.1016/j.jconrel.2007.12.013.
Ishii F, Nii T. Properties of various phospholipid mixtures as emulsifiers or dispersing agents in nanoparticle drug carrier preparations. Colloids Surf B Biointerfaces. Apr. 10, 2005;41(4):257-62. doi: 10.1016/j.colsurfb.2004.12.018.
Barenholz Y, "Doxil®—the first FDA-approved nano-drug: lessons learned," I Control Release, Jun. 10, 2012 ; 160(2): 117-34.
Davies J. A quantitative kinetic theory of emulsion type , I. Physical chemistry of the emulsifying agent, Gas/Liquid and Liquid/Liquid Interface (Proceedings of the International Congress of Surface Activity (1957), pp. 426-438.
Akzo Nobel Surface Chemistry LLC Technical Information bulletin "HLB & Emulsification—Description of Hydrophile, Lipophile Balance and use of HLB in Producing Emulsions," Publication SC-11-02, © 2011 Akzo Nobel Surface Chemistry LLC available at https://www.scribd.com/document/199345154/AkzoNobel-Tb-HlbEmulsions.
Forgiarini A, Esquena J, Gonzalez-Azon C, Solans C. Formation of Nano-emulsions by Low-Energy Emulsification Methods at Constant Temperature. Langmuir. 17. 10.1021/la001362n. Langmuir 2001, 17, 7, 2076-2083. doi: https://doi.org/10.1021/la001362n.
Formiga FR, Fonseca IA, Souza KB, Silva AK, Macedo JP, Araújo IB, Soares LA, Egito ES. Influence of a lipophilic drug on the stability of emulsions: an important approach on the development of lipidic carriers. Int J Pharm. Nov. 1, 2007;344(1-2):158-60. doi: 10.1016/j.ijpharm.2007.05.052.
Salim N, Basri M, Abdullah D, Bin Basri H, Hamidon. Phase Behaviour, Formation and Characterization of Palm-Based Esters Nanoemulsion Formulation containing Ibuprofen. Journal of Nanomedicine & Nanotechnology. doi: 10.4172/2157-7439.1000113.
Lee HS, Morrison ED, Zhang Q, McCormick AV. Cryogenic transmission electron microscopy study: preparation of vesicular dispersions by quenching microemulsions. J Microsc. Sep. 2016;263(3):293-9. doi: 10.1111/jmi.12392. Epub Mar. 3, 2016. PMID: 26937849.
Lee HS, Morrison ED, Frethem CD, Zasadzinski JA, McCormick AV. Cryogenic electron microscopy study of nanoemulsion formation from microemulsions. Langmuir. Sep. 16, 2014;30(36):10826-33. doi: 10.1021/la502207f. Epub Sep. 2, 2014. PMID: 25141294.
Ceve G, Schätzlein A, Richardsen H. Ultradeformable lipid vesicles can penetrate the skin and other semi-permeable barriers unfragmented. Evidence from double label CLSM experiments and direct size measurements. Biochim Biophys Acta. Aug. 19, 2002;1564(1):21-30. doi: 10.1016/s0005-2736(02)00401-7.
Panigrahi L, Pattnaik S, Ghosal SK. The effect of pH and organic ester penetration enhancers on skin permeation kinetics of terbutaline sulfate from pseudolatex-type transdermal delivery systems through mouse and human cadaver skins. AAPS PharmSciTech. Sep. 30, 2005;6(2):E167-73. doi: 10.1208/pt060225.
Mahamongkol H, Bellantone RA, Stagni G, Plakogiannis FM. Permeation study of five formulations of alpha-tocopherol acetate through human cadaver skin. J Cosmet Sci. Mar.-Apr. 2005;56(2):91-10 DOI: 10.1111/j.0142-5463.2005.00275_4.x.
Wilkerson VA. The Chemistry of Human Epidermis: II. The Isoelectric Points of the Stratum Corneum, Hair, and Nails as Determined by Electrophoresis. , J. Biol. Chem ., 1935 , 112 :329-335.
Ali SM, Yosipovitch G. Skin pH: from basic science to basic skin care. Acta Derm Venereol. May 2013;93(3):261-7. doi: 10.2340/00015555-1531.
Bauer, J. (1994). Cell Electrophoresis (1st ed.). CRC Press. https://doi.org/10.1201/9781003069188.
Schambil F, Jost F, Schwuger M. Interfacial and colloidal properties of cosmetic emulsions containing fatty alcohol and fatty alcohol polyglycol ethers. In: Hoffmann, H. (eds) New Trends in Colloid Science. Progress in Colloid & Polymer Science, vol. 73. (1987). Steinkopff. https://doi.org/10.1007/3-798-50724-4_61.
Izquierdo P, Esquena J, Tadros TF, Dederen JC, Feng J, Garcia-Celma MJ, Azemar N, Solans C. Phase behavior and nano-emulsion formation by the phase inversion temperature method. Langmuir. Aug. 3, 2004;20(16):6594-8. doi: 10.1021/la049566h.
Sagitani H. Making homogeneous and fine droplet O/W emulsions using nonionic surfactants. J Am Oil Chem Soc 58, 738-743 (1981). https://doi.org/10.1007/BF02899466.
Solè I, Maestro A, Gonzalez C, Solans C, Gutiérrez JM. Optimization of nano-emulsion preparation by low-energy methods in an ionic surfactant system. Langmuir. Sep. 26, 2006;22(20):8326-32. doi: 10.1021/la0613676.
Fernandez F, André V, Rieger J, Kühnle A. Nano-emulsion formation by emulsion phase inversion, Colloids and Surfaces A: Physicochemical and Engineering Aspects, vol. 251, Issues 1-3, 2004, pp. 53-58 https://doi.org/10.1016/j.colsurfa.2004.09.029.
Porras M, Solans C, González C, Solans C, Gutiérrez J. Properties of water-in-oil (W/O) nano-emulsions prepared by a low-energy emulsification method. Colloids and Surfaces A: Physicochem. Eng. Aspects 324 (2008) 181-188.
Solans C, Solè I, Fernández-Arteaga A, Nolla J, Azemar N, Gutiérrez J, Maestro A, González C, Pey C. Nano-Emulsion Formation by Low-Energy Methods and Functional Properties. Structure and Functional Properties of Colloidal Systems. Taylor and Francis Group, LLC 2010. 457-482.
Salim, Norazlinaliza et al, "Modification of palm kernel oil esters nanoemulsions with hydrocolloid gum for enhanced topical delivery of ibuprofen," International Journal of Nanomedicine, 2012:7 4739-4747.

\* cited by examiner

TRANSPARENT WATER NANOLIPID FLUID (DNLF) DISPERSIONS AND METHOD OF PREPARATION USING A TWIN SCREW EXTRUDER

RELATED APPLICATIONS

This application claims priority to U.S. Provisional Patent Application Ser. No. 63/089,342 filed Oct. 8, 2020 which claims priority to U.S. Non-Provisional Patent Application Ser. No. 16/748,399 filed Jan. 21, 2020, which claims priority to U.S. Provisional Patent Application Ser. No. 62/843,763 filed May 6, 2009, 2009, and to U.S. Provisional Patent Application Ser. No. 62/794,742 filed Jan. 21, 2009, all of which are hereby incorporated by reference in their entirety for all purposes.

This invention provides a method of preparing highly transparent, dense nanolipid fluid (DNLF) dispersions using a twin screw extruder. The inventive DNLF fluids are isotropic fluids which include greater than 25% lipophilic content in the form of lipidic nanoparticles dispersed in a continuous aqueous matrix with turbidity less than 375 nephelometric turbidity units (NTU).

The method includes providing a twin screw extruder having two screws each independently comprising greater than about 26 length/diameter (L/D) of intermeshing conveying elements, wherein the twin screw extruder has two or more temperature control zones, wherein greater than about 40% of the two or more temperature control zones each independently have a temperature less than 35° C., wherein a screw rotation rate is from about 50 rpm to about 250 rpm; introducing a mill base into a first of the two or more temperature control zones of the twin screw extruder, wherein the mill base comprises from about 25 to about 65% lipophilic phase content and the mill base temperature is from 40° C. to 100° C.; collecting the lipid nanoparticle dispersion exiting the extruder wherein the extruded lipid nanoparticle dispersion has a temperature from about 7° C. to about 35° C., a volume average particle size less than 100 nm and turbidity less than 375 NTU.

Preferable highly transparent DNLF fluids are metastable (not at equilibrium). That is, they have kinetic stability but lack thermodynamic stability, meaning that they are not stable as a result of being at their lowest energy state, or in chemical equilibrium but rather as a result of a kinetic barrier to decomposition. In non-equilibrium systems including DNLF dispersions, potential energy is stored. Potential energy in DNLF dispersions can result from Laplace pressure in dispersed nanoparticles that is an effect of surface tension in the interface between nanoparticle and aqueous matrix compressing the interior of the particle. Laplace pressure serves to increase chemical potential for lipid compounds in the nanoparticle which increases bioavailability.

Evidence that a lipid nanoparticle dispersion is not at equilibrium, i.e. that it is a non-equilibrium lipid nanoparticle dispersion includes the observation that the lipid nanoparticle dispersion spontaneously changes over time and that the lipid nanoparticle dispersion does not form spontaneously when all the components of the DNLF composition are mixed and allowed to stand. Typically, transparent equilibrium microemulsions form from mixtures of components within minutes to 72 hours. Equilibrium is temperature dependent, meaning that a system that is at equilibrium at one temperature is not necessarily at equilibrium at a different temperature. As it applies to the present invention, the property of being at equilibrium or not at equilibrium means at between 2° and 25° C.

Highly transparent DNLF dispersions are advantageous because physical properties including Laplace pressure and chemical potential of active ingredients as well as transparency increase when the diameter of the dispersed phase nanoparticles decreases. Highly transparent DNLF fluids are also preferable because clear fluids are considered to be serums which are defined as clear, concentrated cosmetic preparations. Clear serums are especially preferred as products for use on the face.

Preferable DNLF have turbidity as nephelometric turbidity units (NTU) less than 375 NTU. When the turbidity of a lipid nanoparticle dispersion drops below 375 NTU, it becomes possible to read text through a filled bottle about one inch in diameter, and there is consequently an increased perception of quality compared to more turbid preparations. As the turbidity of DNLF dispersions drops below 200 NTU, products appear practically haze free although a Tyndall effect is visible when light passes through. When turbidity is below 100 NTU, DNLF dispersions have the property of being "crystal clear." Such a "crystal clear" appearance is important as it conveys the sense of dissolving or solubilizing active ingredients including hydrophobic therapeutic agents in the form of clear, water soluble serums with high bioavailability and fast absorption.

Heretofore it has been impossible to formulate highly transparent water based serums, that is, water based serums with less than 375 NTU turbidity, that contain more than a small percentage of water immiscible non-amphipathic compounds such as hydrophobic drugs, hydrophobic water insoluble therapeutic agents and water immiscible oils. Consequently, the sum of the concentration of water immiscible non-amphipathic compounds in co-solvent free water based serums with less than 375 NTU turbidity is generally less than 20%. Highly transparent DNLF dispersions as described herein are the only known examples of clear water based serums free of co-solvents having water immiscible non-amphipathic content greater than 20% and turbidity less than 375 NTU. DNLF dispersions of the present invention have greater than 20 weight percent water immiscible non-amphipathic content, aqueous phase concentration greater than 35%, turbidity less than 375 nephelometric turbidity units, lipid nanoparticle volume average particle diameter less than 100 nm and are free of co-solvents.

The invention provides a process for the preparation of a lipid nanoparticle dispersion.

The process comprises:
providing a twin screw extruder having two screws each independently comprising greater than about 26 length/diameter (L/D) of intermeshing conveying elements,
wherein the twin screw extruder has two or more temperature control zones,
wherein greater than about 40% of the two or more temperature control zones each independently have a temperature less than 35° C.,
wherein a screw rotation rate is from about 50 rpm to about 250 rpm;
introducing a mill base into a first of the two or more temperature control zones of the twin screw extruder,
wherein the mill base comprises from about 25 to about 65% lipophilic phase content and the mill base temperature is from 40° C. to 100° C.;
collecting the lipid nanoparticle dispersion exiting the extruder wherein the extruded lipid nanoparticle dispersion has a temperature from about 7° C. to about 35°

C., a volume average particle size less than 100 nm and turbidity less than 375 NTU.

In one embodiment, the mill base includes: from about 10 to about 15% polyethoxylated high HLB surfactant, from about 8 to about 12% low HLB surfactant, from about 20 to about 40% water immiscible non-amphipathic compounds, and from about 35 to about 60% aqueous phase.

In one embodiment, the mill base forms a clear microemulsion between about 60° C. and about 100° C.

In one embodiment the process ΔT is greater than about 35° C.

In one embodiment the process ΔT is greater than about 50° C.

In one embodiment the process ΔT is greater than about 60° C.

In one embodiment the mill base is preheated with a heat exchanger prior to introduction to an extruder in which none of the temperature control zones are heated.

In one embodiment the mill base is processed by passing successively through a heat exchanger and a twin screw extruder with a total residence time less than about 2 minutes.

The invention provides a lipid nanoparticle dispersion with lipophilic concentration greater than 25%, volume average particle size less than 100 nm and turbidity less than 375 NTU. The lipid nanoparticle dispersion includes: one or more polyethoxylated high HLB surfactants selected from the group of laureth-23, ceteareth-20, ceteareth-30, steareth-40, PEG32 stearate, PEG75 stearate, PEG100 stearate, PEG15 hydroxy stearate, PEG40 hydrogenated castor oil, polysorbate 20, and polysorbate 80; one or more low HLB surfactants selected from the group of cetyl alcohol, glyceryl oleate, glyceryl stearate, glyceryl monolinoleate, oleic acid, stearic acid, sorbitan oleate, and soy lecithin; one or more water immiscible oils selected from the group of medium chain triglyceride oil, coconut oil, isopropyl palmitate, isopropyl myristate, methyl decanoate, ethyl myristate, ethyl oleate, mineral oil, orange essential oil, cyclopentasiloxane, poly(dimethyl siloxane), hexadecane, propylene glycol dicaprylate, isododecane, isoeicosane, isohexadecane, soy biodiesel, jojoba oil, cocoyl caprylocaprate, C10-C13 alkane, squalane, and sunflower seed oil; and water. In one embodiment, the lipid nanoparticle dispersion comprises one or more hydrophobic drugs selected from the group of aspirin, benzocaine, ibuprofen, and lidocaine.

In one embodiment, the lipid nanoparticle dispersion comprises one or more hydrophobic therapeutic agents selected from the group of ascorbyl palmitate, birch bark extract, cannabidiol, ubiquinone, cholecalciferol, tetrahydrocannabinol, humulene, myrcene, *Litsea cubeba* oil, limonene, cranberry seed oil, raspberry seed oil, black cumin seed oil, retinyl palmitate, tocopheryl acetate, and tocopherol.

In one embodiment, the lipid nanoparticle dispersion has latent lamellar structure.

In one embodiment, the lipid nanoparticle dispersion is a non-equilibrium lipid nanoparticle dispersion.

In one embodiment, the concentration of water immiscible non-amphipathic compounds is greater than 20%.

In one embodiment, the lipid nanoparticle dispersion additionally comprises a non-ethoxylated high HLB surfactant selected from the group of sodium lauryl sulfate and sodium stearoyl lactylate.

In one embodiment, the lipid nanoparticle dispersion has turbidity less than 250 NTU.

In one embodiment, the lipid nanoparticle dispersion has turbidity less than 125 NTU.

In one embodiment, the lipid nanoparticle dispersion is free of co-solvents.

In one embodiment, the lipid nanoparticle dispersion is free of ibuprofen.

In one embodiment, the lipid nanoparticle dispersion is free of lidocaine.

In one embodiment, the lipid nanoparticles are not vesicular nanoparticles.

In one embodiment, the lipid nanoparticles are not vesicular nanoparticles and the lipid nanoparticle dispersion has latent lamellar structure.

DETAILED DESCRIPTION OF THE INVENTION

The present invention provides a Dense Nanolipid Fluid (DNLF) dispersion for suitable for oral, buccal, sublingual or topical delivery to skin of a mammal. The nanoparticle dispersion includes: one or more hydrophobic therapeutic agents or one or more hydrophobic drugs; one or more surfactants; one or more water immiscible oils; and water. Methods of preparing nanoparticle dispersions by hot melt extrusion are also provided.

The following detailed description shows, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third*

*New International Dictionary*, Merriam-Webster Inc., Springfield, MA, 1993 and *The American Heritage Dictionary of the English Language*, Houghton Mifflin, Boston MA, 1981.

References in the specification to "one embodiment" indicate that the embodiment described may include, for example, a particular feature, structure, or characteristic, but every embodiment may not necessarily include, for example, the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example, about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "administration" refers to a method of placing a device to a desired site. The placing of a device can be by any pharmaceutically accepted means, for example, by swallowing, retaining it within the mouth until the drug has been dispensed, placing it within the buccal cavity, inserting, implanting, attaching, etc. These and other methods of administration are known in the art.

As used herein, "enteral administration" refers to the process by which therapeutic agents are delivered via the human gastrointestinal tract including oral administration, buccal administration, and sublingual administration.

As used herein, the term "oral administration" refers to the process by which drugs are delivered by mouth through the alimentary track.

As used herein, the term "buccal administration" refers to the process by which therapeutic agents are held or applied in the buccal area and diffuse through the oral mucosa directly into the bloodstream.

As used herein, the term "sublingual administration" refers to the process by which therapeutic agents are held or applied to the area under the tongue and diffuse through the oral mucosa directly into the bloodstream.

As used herein, the term "cutaneous administration" refers to the process by which therapeutic agents are applied to the skin.

As used herein, the term "co-solvents" refers to water miscible compounds with molecular weight less than 120 g/mol including alcohols with one or two hydroxyl groups and including aprotic ketones, amides, sulfoxides, pyrrolidones.

As used herein, the term "comprising" or "comprises" is intended to mean that the compositions and methods include the recited elements, but not excluding others.

As used herein, the phrase "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

As used herein, the phrase "consisting of" shall mean excluding more than trace elements of other ingredients and substantial method steps.

As used herein, the terms "consisting essentially of" and "consisting of" are embodied in the term "comprising." In any chemical embodiment described herein, the term "comprising" may be amended, where appropriate, to the recite the terms "consisting essentially of" and "consisting of" As used herein, the term "delivery" refers to the release of a drug from a device including that drug into an environment surrounding the device. The environment into which the drug so released may or may not be the ultimate site of activity for that drug.

In some instances, the released drug may need to be transported to its ultimate site of activity.

As used herein, the term "serum" refers to a transparent water-based fluid preparation.

As used herein, the term "dense nanolipid fluid (DNLF) dispersion" refers to a dispersion of lipid nanoparticles in water with between 25% and 65% of lipophilic content where lipophilic content means the sum of the concentrations of surfactants, water immiscible oils, hydrophobic drugs, and hydrophobic therapeutic agents.

As used herein, the term "water immiscible oil" refers to a chemical compound or mixture of compounds that is liquid at least one temperature between 10° C. and 50° C. that does not form a homogeneous mixture when added to water in any proportion between 1 to 19 and 19 to 1. Water immiscible oils include any of various lubricious, hydrophobic and combustible substances obtained from animal, vegetable and mineral matter. Suitable oils may include, for example, petroleum-based oil derivatives, for example, purified petrolatum and mineral oil. Petroleum-derived oils include, for example, aliphatic or wax-based oils, aromatic or asphalt-based oils and mixed base oils and may include, for example, relatively polar and non-polar oils. "Non-polar" oils are generally oils, for example, petrolatum or mineral oil or its derivatives, which are hydrocarbons and are more hydrophobic and lipophilic compared to synthetic oils, for example, esters, which may be referred to as "polar" oils. It is understood that within the class of water immiscible oils, that the use of the terms "non-polar" and "polar" are relative within this very hydrophobic and lipophilic class, and all of the oils tend to be much more hydrophobic and lipophilic than the water phase, which is used herein.

As used herein, the term "water miscible oil" refers to a chemical compound or mixture of compounds that is liquid at least one temperature between 10° C. and 50° C. that forms a homogeneous mixture when added to water in any proportion between 1 to 19 and 19 to 1.

As used herein, the term "non-equilibrium lipid nanoparticle dispersion" refers to a lipid nanoparticle dispersion that is not at equilibrium at temperatures from 20 to 25° C.

As used herein, the term "microemulsion" refers to a clear or slightly turbid, thermodynamically stable liquid mixture of surfactants, lipophilic and hydrophilic phases that are optically isotropic when viewed in unpolarized light and are prepared by simple mixing of the components or simple mixing and heating of the components.

As used herein, "lipid nanoparticle" refers to an assemblage of surfactants and water immiscible oils that optionally comprises a hydrophobic therapeutic agent.

As used herein, the term "dispersion of lipid nanoparticles in water" refers to a dispersion of lipid particles in water with a volume average particle size less than 150 nm.

As used herein, the term "dermis" refers to the sensitive connective tissue layer of the skin located below the epidermis, containing nerve endings, sweat and sebaceous glands, and blood and lymph vessels. Histologically, the dermis consists of a papillary layer and a reticular layer. The papillary layer contains the vessels and nerve endings supplying the epidermis. The reticular consists predominantly of elastic fibers and collagen.

As used herein, the term "diluent" refers to a pharmacologically inert substance that is nevertheless suitable for human consumption that serves as an excipient in the inventive dosage form. A diluent serves to dilute the API in the inventive dosage form, such that tablets of a typical size can be prepared incorporating a wide range of actual doses of the API.

As used herein, the term "surfactant" refers to an agent that facilitates the formation of a dispersion of one or more internal phases in a continuous phase. Examples of such dispersions include dispersions of lipid nanoparticles, DNLF dispersions, suspensions and emulsions, wherein the continuous phase may be water, for example, and the internal phase is a solid, a water-immiscible liquid, or a lipid nanoparticle, respectively. Thus, dispersing agents may include suspending agents and emulsifying agents.

As used herein, the term "water immiscible non-amphipathic compound" refers a molecule that is not miscible with or soluble in water and is not dispersible in water in the absence of a surfactant that comprises a water insoluble hydrocarbon chain or a hydrophobic group with six or more carbon atoms Water immiscible non-amphipathic compounds include water immiscible oils, hydrophobic drugs, and hydrophobic therapeutic agents.

As used herein, the term "dosage form" refers to a physical and chemical composition of a therapeutic agent that is adapted for administration to a patient in need thereof.

As used herein, the phrase "medium chain triglyceride oil" refers to medium chain triglyceride oil (CAS No. 73398-61-5 or CAS No. 438544-49-1) and to fractionated coconut oil, which is also called capric/caprylic triglyceride (CAS No. 65381-09-1).

As used herein, the term "drug" refers to a therapeutic agent or a diagnostic agent and includes any substance, other than food, used in the prevention, diagnosis, alleviation, treatment, or cure of a disease. *Stedman's Medical Dictionary*, 25$^{th}$ Edition (1990). The drug can include, for example, any substance disclosed in at least one of: *The Merck Index*, 13$^{th}$ Edition, 1998, published by Merck & Co., Rahway, N.J.; Pei-Show Juo, *Concise Dictionary of Biomedicine and Molecular Biology*, (1996); *U.S. Pharmacopeia Dictionary*, 2000 Edition; and *Physician's Desk Reference*, 2001 Edition.

As used herein, the term "hydrophobic drug" refers to a drug that has a log P value greater than 1.

As used herein, the term "edible" refers to substance, chemical compound or ingredient that is listed on the US Food and Drug Administration Inert Ingredient Guide (IIG) and/or approved for direct addition to food for humans (21CFR Part 172).

As used herein, the term "an effective amount" refers to an amount sufficient to effect beneficial or desired results. An effective amount can be administered in one or more administrations, applications, or dosages. Determination of an effective amount for a given administration is well within the ordinary skill in the pharmaceutical arts.

As used herein, the term "enantiomeric excess" refers to the degree to which a sample of a compound of a chiral substance contains one enantiomer in greater amounts than the other. Percent enantiomeric excess is defined as =100*([enantiomer 1]−[enantiomer 2])/([enantiomer 1]+[enantiomer 2]).

As used herein, the term "epidermis" refers to the outer, protective, nonvascular layer of the skin of vertebrates, covering the dermis. The epidermis consists histologically of five layers, i.e., the stratum corneum, the stratum lucidum, the stratum granulosum, the stratum spinosum, and the stratum basale.

As used herein, the term "essential oil" refers to a volatile oil derived from the leaves, stem, flower or twigs of plants or synthetically-made compounds that have the same chemical attributes. The essential oil usually carries the odor or flavor of the plant. Chemically, each plant essential oil or derivative thereof, which may be extracted from natural sources or synthetically made, generally contains, as a major constituent, an acyclic monoterpene alcohol or aldehyde, a benzenoid aromatic compound containing at least one oxygenated substituent or side chain, or a monocarbocyclic terpene generally having a six-membered ring bearing one or more oxygenated substituents.

As used herein, the term "essential oil" includes derivatives thereof, including racemic mixtures, enantiomers, diastereomers, hydrates, salts, solvates, metabolites, analogs, and homologs Essential oils, their chemistry and plant families are known in the art. See, for example, S. Price, Aromatherapy Workbook—Understanding Essential Oils from Plant to Bottle, (HarperCollins Publishers, 1993; J. Rose, The Aromatherapy Book—Applications & Inhalations (North Atlantic Books, 1992); and The Merck Index (12th Ed. 1996), each of which is incorporated herein by reference.

As used herein, the term "HLB" refers to Hydrophile-Lipophile Balance, which is an empirical expression for the relationship of the hydrophilic ("water-loving") and hydrophobic ("water-hating") groups of a surfactant.

As used herein, the term "latent lamellar structure" refers to the characteristic of a lipid nanoparticle dispersion without observable lamellar structure to develop observable lamellar structure when the lipid nanoparticle dispersion is heated or when volatile components of the nanoparticle dispersion are lost from the nanoparticle dispersion by evaporation.

As used herein, the phrase "low hydrophile-lipophile-balance (HLB) surfactant" refers to a surfactant with an hydrophile-lipophile-balance (HLB) value of less than about 10.

As used herein, the phrase "high hydrophile-lipophile-balance (HLB) surfactant" refers to a surfactant with an hydrophile-lipophile-balance (HLB) value of equal to or greater than about 14.

As used herein, the phrase "polyethoxylated high hydrophile-lipophile-balance (HLB) surfactant" refers to a surfactant with an hydrophile-lipophile-balance (HLB) value of equal to or greater than about 14 that comprises a polymer or oligomer whose repeat unit is derived from ethylene oxide.

As used herein, the phrase "medium hydrophile-lipophile-balance (HLB) surfactant" refers to a surfactant with an hydrophile-lipophile-balance (HLB) value of equal between about 10 and about 14.

As used herein, the term "immersing" refers to dipping, plunging, or sinking into a liquid.

As use herein, the term "immiscible" refers to liquids that will not mix or remain mixed with each other, although at certain conditions, for example, high temperatures, they might mix, but any such mixture will typically be thermodynamically unstable and will typically separate into distinct phases at lower temperatures.

As used herein, the terms "include," "for example," "such as," and the like are used illustratively and are not intended to limit the present invention.

As used herein, the terms "individual," "host," "subject," and "patient" are used interchangeably, and refer to a mammal, including, but not limited to, primates, including simians and humans.

As used herein, the term "infection" refers to the invasion of the host by germs that reproduce and multiply, causing disease by local cell injury, release of poisons, or germ-antibody reaction in the cells. The infection can be in a mammal (e.g., human).

As used herein, the term "lipid" refers fats and fat-derived materials. See, e.g., Concise Chemical and Technical Dictionary, 4$^{th}$ Edition, Chemical Publishing Co., Inc., p. 704, New York, NY (1986).

As used herein, the term "liquid" refers to a substance that undergoes continuous deformation under a shearing stress. See, e.g., Concise Chemical and Technical Dictionary, 4$^{th}$ Edition, Chemical Publishing Co., Inc., p. 707, New York, NY (1986).

As used herein, "lipophilic content" means the sum of the concentrations of all surfactants, water immiscible oils, hydrophobic drugs, and hydrophobic therapeutic agents.

As used herein, "aqueous phase content" means the sum of the concentrations of water, water miscible oils, water soluble salts, water soluble compounds, and water soluble therapeutic agents excluding all surfactants As used herein, the term "log P" refers to the base 10 logarithm of the equilibrium octanol-water partition coefficient of a solute, that is, log P=log([solute concentration in octanol]/[solute concentration in water]) when the octanol and water solutions are in contact and at equilibrium.

As used herein, the term "mammal" refers to any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, for example, horses, cattle, sheep, and goats, and research and domestic species, including dogs, cats, mice, rats, guinea pigs, and rabbits.

As used herein, the phrase "medium chain triglyceride oil" refers to the chemical with CAS Number 438544-49-1.

As used herein, the phrase "mill base" refers to a mixture comprising between 25% and 65% of lipophilic content where lipophilic content means the sum of the concentrations of surfactants, water immiscible oils, hydrophobic drugs, and hydrophobic therapeutic agents that is liquid at at least one temperature from 40° C. to 100° C.

As used herein, the term "molecular weight" refers to a weight-average molecular weight, as is well known in the art.

As used herein, the terms "optional" or "optionally" mean that the subsequently described event or condition may but need not occur, and that the description includes instances where the event or condition occurs and instances in which it does not.

As used herein, the term "patient" refers to a warm-blooded animal, and preferably a mammal, for example, a cat, dog, horse, cow, pig, mouse, rat, or primate, including a human.

As used herein, the term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications, for example, *The United States Pharmacopeia* describe the analytical criteria to assess the pharmaceutical acceptability of numerous ingredients of interest.

As used herein, the term "pharmacologically active agent" refers to a chemical compound, complex or composition that exhibits a desirable effect in the biological context, i.e., when administered to a subject. The term includes pharmacologically active, pharmaceutically acceptable derivatives of those active agents specifically mentioned herein, including, but not limited to, salts, esters, amides, prodrugs, active metabolites, isomers, analogs, crystalline forms, hydrates, and the like.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

It will be understood that, although the terms first, second, etc., may be used herein to describe various elements, these elements should not be limited by these terms. These terms are only used to distinguish one element from another. For example, a first element could be termed a second element, and, similarly, a second element could be termed a first element without departing from the teachings of the disclosure.

As used herein, the terms "prevent," "preventative," "prevention," "protect," and "protection" refer to medical procedures that keep the malcondition from occurring in the first place. The terms mean that there is no or a lessened development of disease or disorder where none had previously occurred, or no further disorder or disease development if there had already been development of the disorder or disease.

As used herein, the term "%" or "percent" refers to weight percent (%).

As used herein, the term "polysaccharide" refers to biological carbohydrate molecules consisting of carbon (C), hydrogen (H) and oxygen (O) formed from linking saccharides through glycosidic bonds.

As used herein, the phrase "twin screw extruder" refers to a machine consisting of two screws which are mounted on shafts and rotate in in a fixed closed housing.

As used herein, the phrase "length/diameter" which is abbreviated L/D refers to the ratio of a unit of distance parallel to the axis of the barrel of a twin screw extruder divided by the diameter of one of the screws.

As used herein, the phrase "temperature control zone" refers to a length portion of the barrel of a twin screw extruder in which the barrel temperature is controlled by heating or cooling.

As used herein, the phrase "intermeshing conveying element" refers to a helical portion of a first extruder screw capable to intermesh with an opposing portion of a second extruder screw so as to convey a liquid parallel to the axis of the first extruder screw in such a way that the two opposing extruder screw portions are self-wiping.

As used herein, the phrase "process ΔT" refers to the difference between the greater of the mill base temperature as introduced to the extruder or the highest extruder zone temperature minus lowest extruder zone temperature.

As used herein, the term "purified" compound refers to a compound that is present in a given quantity at a concentration of at least 50%, 60%, 70%, 80%, 90% and intermediate values thereof and all in weight percent (%). For example, an isolated compound may be present at 51%, 52%, 53%, 54% and the like. Preferably the compound is present at 90% to 95% and intermediate values thereof. More preferably the compound is present at 95% to 99%, and intermediate values thereof. Even more preferably the compound is present at 99% to 99.9% and intermediate values thereof. Most preferably the compound is present at greater than 99.9% of a given quantity.

As used herein, the term "skin" refers to the external tissue layer in humans and animals consisting of epidermis and dermis.

As used herein, the phrase "room temperature" refers to a temperature in the range of about 20° C. to about 30° C.

As used herein, the phrase "subcutaneous tissue layer" refers to a tissue layer located below the skin. This tissue layer is typically characterized by a loose meshwork of connective tissue, for example, collagen and elastic fibers. It is rich in small vessels, e.g., arterioles and venoles, and capillaries.

As used herein, the term "therapeutic agent" refers to a chemical compound, complex or composition that exhibits a desirable effect in the biological context, i.e., when administered to a subject.

As used herein, the term "hydrophobic therapeutic agent" refers to a therapeutic agent that has a log P value greater than 1.

As used herein, the term "water soluble therapeutic agent" refers to a therapeutic agent that has a log P value less than 1 and solubility in water at 25° C. greater than 0.5 weight percent.

As used herein, the term "therapeutic composition" refers to an admixture with an organic or inorganic carrier or excipient, and can be compounded, for example, with the usual non-toxic, pharmaceutically acceptable carriers for tablets, pellets, capsules, suppositories, solutions, emulsions, suspensions, or other form suitable for use.

As used herein, the term "therapeutically effective amount" is intended to include, for example, an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example, by Chou and Talalay, *Adv. Enzyme Regul.*, 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, the terms "therapy," and "therapeutic" refer to producing a desirable effect in the biological context including "treatment" or "prevention," thus, agents that either treat damage or prevent damage are "therapeutic."

As used herein, the phrase "therapeutic kit" refers to a collection of components that can be used in a medical treatment.

As used herein, the phrase "therapeutic dosage" refers to a dosage considered to be sufficient to produce an intended effect.

As used herein, the phrase "therapeutically effective modality" refers to a manner in which a medical treatment is performed and is considered to be sufficient to produce an intended effect.

As used herein, the term "tissue" refers to an organized biomaterial usually composed of cells.

As used herein, the term "topically" refers to application of the compositions of the present invention to the surface of the skin and mucosal cells and tissues (e.g., alveolar, buccal, lingual, sublingual, masticatory, or nasal mucosa, and other tissues and cells, which line hollow organs or body cavities).

As used herein, the terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

As used herein, the term "treatment," covers any treatment of a disease in a mammal, particularly in a human, and includes: (a) preventing the disease from occurring in a subject, which may be predisposed to the disease but has not yet been diagnosed as having it; (b) inhibiting the disease, i.e., arresting its development; and (c) relieving the disease, i.e., causing regression of the disease.

As used herein, "g" denotes microgram, "mg" denotes milligram, "g" denotes gram, "L" denotes microliter, "mL" denotes milliliter, "L" denotes liter, "nM" denotes nanomolar, "μM" denotes micromolar, "mM" denotes millimolar, "M" denotes molar, and "nm" denotes nanometer.

Concentrations, amounts, etc., of various components are often presented in a range format throughout this disclosure. The description in range format is merely for convenience and brevity and should not be construed as an inflexible limitation on the scope of the claimed invention. Accordingly, the description of a range should be considered to have specifically disclosed all the possible sub ranges as well as individual numerical values within that range. For example, description of a range such as 1% to 8% should be considered to have specifically disclosed sub ranges such as 1% to 7%, 2% to 8%, 2% to 6%, 3% to 6%, 4% to 8%, 3% to 8% etc., as well as individual numbers within that range, such as, 2%, 5%, 7% etc. This construction applies regardless of the breadth of the range and in all contexts throughout this disclosure.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

The invention illustratively disclosed herein suitably may be practiced in the absence of any element which is not specifically disclosed herein.

The present invention provides a Dense Nanolipid Fluid (DNLF) dispersion for suitable for oral, buccal, sublingual or topical delivery to skin of a mammal. The lipid nanoparticle dispersion includes: one or more hydrophobic therapeutic agents having a log P>1; one or more polyethoxylated high hydrophile-lipophile-balance (HLB) surfactants; one or more low hydrophile-lipophile-balance (HLB) surfactants each independently having a hydrophile-lipophile-balance (HLB) value less than about 10; one or more water immiscible oils; and water.

Suitable hydrophobic therapeutic agents may include, for example, (1) oil soluble vitamins and provitamins such as retinol (Vitamin A), retinyl palmitate (Vitamin A), retinyl sunflowerate (Vitamin A), ascorbyl palmitate (vitamin C), tetrahexyldecyl ascorbate (vitamin C), cholecalciferol (Vitamin D3), ergocalciferol (vitamin D2), tocopherol (Vitamin E), and tocopheryl acetate (Vitamin E), phylloquinone and derivatives (Vitamin K), and coenzyme Q (ubiquinone); (2) Essential oils extracted from plants through distillation (via steam and/or water) or mechanical methods such as cold pressing, such as frankincense essential oil, lavender essential oil, raspberry seed oil, cranberry seed oil, tomato seed oil, black cumin seed oil, hemp flower extract, hemp seed oil, tea tree essential oil, *Litsea cubeba* oil, orange essential oil, peppermint essential oil, lemongrass essential oil, eucalyptus essential oil, rosemary essential oil, cedarwood essential oil, clove essential oil, bergamot essential oil, *Arnica* flower essential oil, omega-3 algae oil, blackberry seed oil, broccoli seed oil, carrot seed oil, cucumber seed oil, flaxseed oil, grape seed oil, pumpkin seed oil, pomegranate seed oil and camphor essential oil; (3) Terpenoids, diterpenoids and polyterpenoids and derivatives thereof including methyl salicylate, birch bark extract, geraniol, limonene, camphor, and menthol; (4) Cannabinoids such as cannabidiol and tetrahydrocannabinol; (5) Polyphenol compounds such as reservatrol, ellagic acid, tannic acid; and (6) Therapeutic fatty acids derived from castor oil such as ricinoleic acid and undecylenic acid.

Preferably, the one or more hydrophobic therapeutic agents are selected from the group cannabidiol, tocopherol, retinyl palmitate, ascorbyl palmitate, cholecalciferol, tocopheryl acetate, coenzyme Q, cold pressed seed oils, humulene, myrcene, *Arnica* flower essential oil, *Litsea cubeba* oil, orange essential oil, and tetrahydrocannabinol.

Suitable hydrophobic drugs may include, for example, aspirin, atropine, benzocaine, cortisol, cortisone, diclofenac, diflusinal, dronabinol, estradiol, flurbiprofen, haloperidol, hydrocortisone, ibuprofen, S-ibuprofen, ketoprofen, ketorolac, lidocaine, minoxidil, naproxen, nicotine, penicillin V, prednisone, progesterone, salicylic acid, and sulindac.

Preferably, the one or more hydrophobic drugs are selected from the group consisting of lidocaine, benzocaine, ibuprofen, and aspirin.

Suitable polyethoxylated high hydrophile-lipophile-balance (HLB) surfactants may include, for example, one or more polyethoxylated high hydrophile-lipophile-balance (HLB) surfactants each independently having a hydrophile-lipophile-balance (HLB) value of equal to or greater than about 14.
derived from addition of about 15 to about 100 moles of ethylene oxide to fatty alcohols such as lauryl alcohol, cetyl alcohol, oleyl alcohol, stearyl alcohol, and isotridecyl alcohol which may be referred to as alcohol ethoxylates, polyoxyethylene alkyl ethers, and polyoxyethylated fatty alcohols including laureth-23, ceteth-20, ceteareth-20, ceteareth-25, ceteareth-30, oleth-20, steareth-20, steareth-40, and steareth-100 which are available, for example, as commercial products including Brij® L23, Brij® CS20, Brij® 020, Brij® S20 and Brij® S100. Suitable polyethoxylated high hydrophile-lipophile-balance (HLB) surfactants may include, for example, one or more polyethoxylated high hydrophile-lipophile-balance (HLB) surfactants each independently having a hydrophile-lipophile-balance (HLB) value of equal to or greater than about 14 derived from addition of about 15 to about 100 moles of ethylene oxide to saturated or unsaturated fatty acids which may be referred to as polyethylene glycol carboxylates, poly(oxyethylene) carboxylates and poly(ethylene oxide) carboxylate esters including poly(ethylene oxide) laurate esters, poly(ethylene oxide) oleate esters, and poly(ethylene oxide) stearate esters, such as PEG-15 hydroxystearate, PEG-20 laurate, PEG-20 oleate, PEG-20 stearate, PEG-32 stearate, PEG-40 stearate, and PEG-100 stearate which are available, for example, as commercial products including Kolliphor HS15, Myrj® S40 and Myrj® S100. Suitable polyethoxylated high hydrophile-lipophile-balance (HLB) surfactants may include, for example, one or more polyethoxylated high hydrophile-lipophile-balance (HLB) surfactants each independently having a hydrophile-lipophile-balance (HLB) value of equal to or greater than about 14 derived from addition of about 15 to about 100 moles of ethylene oxide to fatty acid sorbitan esters which may be referred to as polyoxyethylene sorbitan carboxylates, such as polysorbate 20, polysorbate 40, polysorbate 60, and polysorbate 80 which are available, for example, as commercial products including Tween® 20, Tween® 40, Tween® 60, and Tween® 80. Suitable polyethoxylated high hydrophile-lipophile-balance (HLB) surfactants may include, for example, one or more polyethoxylated high hydrophile-lipophile-balance (HLB) surfactants each independently having a hydrophile-lipophile-balance (HLB) value of equal to or greater than about 14 derived from addition of about 15 to about 100 moles of ethylene oxide to fatty acid glycerin esters which may be referred to as polyethylene glycol glyceryl carboxylates such as PEG-30 glyceryl cocoate, poly(oxyethylene) glyceryl monolaurate and poly(oxyethylene) glyceryl monostearate, which are available, for example, as commercial products including Jeechem GL-30 and Jeechem GC-30. Suitable polyethoxylated high hydrophile-lipophile-balance (HLB) surfactants may include, for example, one or more polyethoxylated high hydrophile-lipophile-balance (HLB) surfactants each independently having a hydrophile-lipophile-balance (HLB) value of equal to or greater than about 14 derived from addition of about 15 to about 100 moles of ethylene oxide to castor oil or hydrogenated castor oil such as PEG-25 castor oil ethoxylate, PEG-40 castor oil ethoxylate, PEG-60 castor oil ethoxylate, hydrogenated PEG-25 castor oil ethoxylate, hydrogenated PEG-40 castor oil ethoxylate, and hydrogenated PEG-60 castor oil ethoxylate, which are available, for example, as commercial products including Cremophor® RH40.

Preferably, the one or more polyethoxylated high hydrophile-lipophile-balance (HLB) surfactants are selected from the group consisting of ceteareth-20, laureth-23, steareth-40, PEG-100 stearate; PEG-75 stearate, PEG-32 stearate, polysorbate 20, and polysorbate 80, PEG-40 hydrogenated castor oil, and PEG-15 hydroxy stearate.

Suitable one or more low hydrophile-lipophile-balance (HLB) surfactants each independently having a hydrophile-lipophile-balance (HLB) value less than about 10 may include, for example (1) Fatty acid esters including saccharide residues including sorbitan monolaurate, sorbitan monopalmitate, sorbitan stearate, sorbitan oleate, sorbitan isostearate, sorbitan sesquioleate, sorbitan trioleate, and sorbitan tristearate, which are available, for example, as commercial products including Span® 120, Span® 20, Span® 60, Span® 80, Span® 83, and Span® 85; (2) fatty acid glycerides, for example, glycerol monooleate, glyceryl monostearate, glycerol dioleate, glycerol distearate, which are available, for example, as commercial products including Jeechem GMS-D and Jeechem GMIS; (3) fatty alcohol ethoxylates, fatty alcohol propoxylates, and fatty alcohol ethoxylate propoxylates for example, oleth-2, ceteareth-2, and lauryl alcohol 3 mole ethoxylate/6 mole propoxylate, which are available, for example, as commercial products including Brij® L4, Brij®O5, Brij®S2, and Alkomol® L 306; (4) fatty alcohols such as lauryl alcohol, cetyl alcohol, stearyl alcohol and oleyl alcohol; and (5) Saturated or unsaturated, linear or branched aliphatic $C_8$ to $C_{22}$ carboxylic acid functional compounds including fatty acids derived from the saponification of vegetable and animal fats and oils, for example, octanoic acid, coconut fatty acid, oleic acid, ricinoleic acid, stearic acid, and carboxylic acid terminated short chain (e.g., n=4) polymers of ricinoleic acid and mixtures of such surfactants; (6) phospholipid compounds, for example, phosphatidyl choline, phosphatidylethanolamine, and phosphatidylinositol and compositions which include mixtures of these, for example, lecithins. Phospholipid products are available, for example, as commercial products including Phospholipon® 90G, Phospholipon® 90H, Alcolec® XTRA-A, Alcolec® PC 75 and Sunlipon® 65.

Preferably, the one or more low hydrophile-lipophile-balance (HLB) surfactants are selected from the group consisting of stearic acid, glyceryl stearate, sorbitan oleate, sorbitan stearate, cetyl alcohol, glyceryl monolinoleate, glyceryl oleate, soy lecithin, and dioleyl phosphatidyl choline.

Suitable water immiscible oils include, for example (1) hydrocarbons, for example, mineral oil, isoparaffin, isohexadecane, isohexadecane, poly(alpha olefins), squalane and squalene, hydrogenated oligomers of propene, butane, and isobutylene, cycloaliphatic compounds, and alkylated aromatic compounds, for example, alkylated naphthalenes; (2) Siloxane polymers and oligomers, for example, cyclopentasiloxane, poly(dimethyl siloxane), and poly(methyl phenyl siloxane); (3) Monoesters including fatty acid esters with lower aliphatic alcohols methanol, ethanol and isopropanol; fatty acid esters with aromatic compounds, and fatty acid esters with fatty alcohols for example methyl decanoate, methyl myristate, biodiesel, isopropyl myristate, and isopropyl palmitate, cocoyl caprylocaprate, cetyl palmitate and decyl oleate; (4) Polyesters including: fatty acid esters of polyols including triglycerides, sucrose polyesters, trimethylol propane triesters, pentaerythritol and dipentaerythritol polyesters, and glycol or poly(alkylene glycol) diesters; and fatty alcohol esters of di and polyacid compounds, for example, coconut oil, hemp seed oil, fractionated coconut oil, sunflower seed oil, olive oil, canola oil, medium chain triglyceride (MCT) oil, tricaprin, tridecanoin, triolein, and tristearin, propylene glycol dicaprylate/dicaprate and propylene glycol dimyristate; and (6) Sterols and sterol esters, for example, lanolin.

Preferably, the one or more water immiscible oils are selected from the group consisting of isopropyl myristate, medium chain triglyceride oil, hemp seed oil, mineral oil, cocoyl caprylocaprate, methyl decanoate, cyclo pentasiloxane, mineral oil, soy biodiesel, medium chain triglyceride oil, isopropyl palmitate, hexadecane, isoeicosane, coconut oil, dimethicone, squalane, isohexadecane, isododecane, C23-C15 linear alkane, propylene glycol dicaprylate, ethyl myristate, ethyl oleate, C13-C15 alkane, and jojoba oil.

In addition to polyethoxylated high HLB surfactants, low HLB surfactants and water immiscible oils compositions of the present invention can optionally include high HLB surfactants that do not contain ethylene glycol residues. Suitable high HLB non-ethoxylated surfactants include: (1) fatty ether mono-, di- and oligoglycosides containing a ether bond between a fatty alcohol and a mono-, di- and oligoglycosides, alkyl polyglucosides, and alkylpolyglycosides such as decyl glucoside, cocoglucoside, poly(D-glucopyranose) ether with (C8-C14) linear primary alcohols, and xylityl caprate/caprylate which are available, for example, as commercial products including Plantacare® 2000 UP and Giorbis GiO™—103; (2) polyglyceryl fatty acid monoesters with such as triglycerol monolaurate, tetraglycerol monolaurate, triglycerol monooleate, tetraglycerol monooleate, triglycerol monostearate, tetraglycerol monostearate; (3) mono- and di-esters of glycerin with linear or branched long chain (greater than about 8 carbon atoms) fatty acids further esterified with short chain monocarboxylic acids and salts thereof, for example, sodium stearoyl lactylate; (4) Saturated or unsaturated, linear or branched aliphatic $C_8$ to $C_{22}$ alkyl sulfonate and sulfate compounds, for example, octanesulfonic acid, sulfuric acid ester with lauryl alcohol, and salts thereof such as sodium lauryl sulfate; (5) Saturated or unsaturated, linear or branched aliphatic $C_8$ to $C_{22}$ ethoxylated alkyl sulfonate and sulfate compounds, for example, sulfuric acid ester with the product of addition of four moles of ethylene oxide to lauryl alcohol, and salts thereof such as sodium laureth sulfate; (6) sulfonated succinic acid esters with saturated or unsaturated, linear or branched aliphatic $C_8$ to $C_{22}$ alcohols, for example, the bis(2-ethylhexyl) ester of sulfosuccinic acid and the lauryl poly(ethylene oxide) ester of sulfosuccinic acid, or a mixture of these surfactants; (7) esters of lactic acid or lactic acid oligomers with fatty acids and salts thereof such as sodium stearoyl-2-lactylate; (8) sulfonates of benzene, cumene, toluene and alkyl substituted aromatic compounds and salts thereof, for example, dodecyl benzene sulfonic acid, or a mixture of these surfactants; (9) carboxylates of alcohol ethoxylates, alcohol propoxylates, alcohol ethoxylate propoxylates and ethoxylated linear and branched alkylphenol compounds and salts thereof, for example, poly(ethylene oxide) tridecyl alcohol ether carboxylic acid and sodium poly(ethylene oxide) lauryl ether carboxylate, or a mixture of these surfactants; (10) long chain (greater than about 8 carbon atoms) acyl amino acids, for example, acyl glutamates, acyl peptides, acyl sarcosinates, acyl taurates, salts thereof, and mixtures of these surfactants; (11) Saturated or unsaturated, linear or branched aliphatic $C_8$ to $C_{22}$ alkyl amido propyl (dimethyl ammonio) acetate compounds, for example, lauramidopropyl betaine and stearamidopropyl betaine, and mixtures of these surfactants; (12) Sophorolipids, which consist of a hydrophobic fatty acid tail of a hydroxylated 16 or 18 carbon atom fatty acid, which is β-glycosidically linked to a hydrophilic sophorose head, including free acid (open) and internally esterified (lactonic) forms and acetylated forms (acetylated on the 6'- and/or 6"-positions; and (13) Rhamnolipids including mono-rhamnolipids, which consist of one or two 3-(hydroxyalkanoyloxy) alkanoic acid tails and a single rhamnose head and di-rhamnolipids, which consist of one or two 3-(hydroxyalkanoyloxy) alkanoic acid tails and two rhamnose heads, including mixtures of compounds produced by *Pseudomonas* and *Burkholderia* bacterial species, for example, *Pseudomonas aeruginosa* and *Burkholderia plantarii*.

Preferably, the one or more non-polyethoxylated high hydrophile-lipophile-balance (HLB) surfactants selected from the group consisting of sodium stearoyl lactylate and sodium lauryl sulfate.

The lipid nanoparticle dispersion may also include, for example, one or water soluble polymers or gums, including: (1) Polysaccharides such as dextrins, gums, including maltodextrin, cyclodextrin, hyaluronic acid, xanthan gum, guar gum, and water dispersible or water-soluble starches; (2) Water soluble cellulose derivatives including cellulose ethers such as methyl cellulose, carboxymethyl cellulose, hydroxypropyl methyl cellulose, and carboxyethyl cellulose; (3) Poly(acrylic) acid and salts thereof including Carbomer 940, and sodium carbomer such as Neutragel DA (product of 3V Sigma USA, Georgetown SC); (4) Acrylates/Vinyl Crosspolymers such as Rapidgel EZ1 (product of 3V Sigma USA); and (5) Poly(vinyl pyrrolidone).

Preferably, the one or more water soluble polymers is hyaluronic acid.

The nanoparticle dispersion may also include, for example, one or more cryoprotectants that prevent the freezing of nanoparticle dispersions, or prevents decomposition of nanoparticle dispersions during freezing. Preferred cryoprotectants are water miscible or water soluble compounds including glycerin, propylene glycol, ethylene glycol, diethylene glycol, diethylene glycol monoethyl ether, sucrose, sorbitol, trehalose, and dimethyl sulfoxide (DMSO).

Preferably, the one or more cryoprotectants is glycerin or diethylene glycol monoethyl ether.

The lipid nanoparticle dispersion may also include, for example, one or more water soluble therapeutic agents such as acylclovir, arbutin, ascorbic acid, barbaloin, caffeic acid, caffeine, cobalamin, cyanocobalamin, ferulic acid, folic acid, gallic acid, hydroquinone, kojic acid, niacin, niacinamide, panthenol, pantothenic acid, para aminobenzoic acid, pyridoxine, riboflavin, salicin, streptomycin, tannic acid, thiamine, and water soluble peptides.

Preferably, the one or more water soluble therapeutic agents are selected from the group consisting of caffeine, niacinamide, arbutin, and kojic acid.

The lipid nanoparticle dispersion may also include, for example, one or more preservative additives such as antioxidants, chelating agents, acidulants, and antimicrobial agents. Useful antioxidants include, for example, butylated hydroxyl toluene (BHT). Useful chelating agents include, for example, phosphates, ethylenediaminetetraacetic acid and salts thereof, sodium phytate, and nitrilotriacetic. Useful antimicrobial agents include, for example, sodium benzoate, and mixtures of phenoxy ethanol with caprylyl glycol such as Optiphen, product of Ashland Chemicals and Jeechem CAP-4, product of Jeen.

Preferably, the one or more preservative additives are selected from the group consisting of sodium phytate, sodium benzoate, phenoxy ethanol, and caprylyl glycol. Preferred highly transparent lipid nanoparticle dispersions have latent lamellar structure, that is, the characteristic of a lipid nanoparticle dispersion without observable lamellar structure to develop observable lamellar structure when the lipid nanoparticle dispersion is heated or when volatile components of the nanoparticle dispersion are lost from the nanoparticle dispersion by evaporation. Latent lamellar structure can be discerned as birefringence in a stirred lipid nanoparticle dispersion that is subjected to heating, evaporation, or both. Latent lamellar structure in a lipid nanoparticle dispersion can also be discerned as a visibly apparent negative peak in a plot of conductivity vs temperature or as a positive peak in the first derivative plot of normalized conductivity versus temperature, i.e. d(normalized conductivity)/dT, with a peak amplitude greater than about $0.1°$ $C.^{-1}$ for a lipid nanoparticle dispersion that is heated and stirred. Normalized conductivity for a lipid nanoparticle dispersion is the conductivity of the lipid nanoparticle dispersion at the temperature of observation divided by the maximum observed conductivity in the temperature range between 40° C. and 95° C. The presence of latent lamellar structure in lipid nanoparticle dispersions can also be discerned as layer spacing (d-spacing) from small angle x-ray scattering (SAXS) or from neutron diffraction. Direct observation of lamellar structure, for example as vesicular nanoparticles, is possible by diluting DNLF dispersions with water and imaging using cryogenic transmission electron microscopy as described by Lee et al., Langmuir, 2004, Sep. 16; 30(36):10826-33. DOI: 10.1021/la502207f.

EXAMPLES

These examples exemplify making highly transparent nanolipid fluids in a twin screw extruder comprising one or more water immiscible oils including medium chain triglyceride oil, coconut oil, isopropyl palmitate, isopropyl myristate, methyl decanoate, ethyl myristate, ethyl oleate, mineral oil, cyclopentasiloxane, poly(dimethyl siloxane), hexadecane, propylene glycol dicaprylate, isododecane, isoeicosane, isohexadecane, soy biodiesel, jojoba oil, cocoyl caprylocaprate, C10-C13 alkane, *Litsea cubeba* oil, squalane, cranberry seed oil, raspberry seed oil, black cumin seed oil, and sunflower seed oil; and one or more hydrophobic drugs including ibuprofen, lidocaine, benzocaine and aspirin and/or one or more hydrophobic therapeutic agents including ascorbyl palmitate (vitamin C palmitate), aspirin, birch bark extract, benzocaine, cannabidiol, coenzyme Q (ubiquinone), humulene, myrcene, limonene, cholecalciferol (vitamin D3), tetrahydrocannabinol, orange essential oil, ibuprofen, lidocaine, retinyl palmitate (vitamin A palmitate), tocopheryl acetate (vitamin E acetate), and tocopherol (vitamin E).

In the following examples, particle size was measured Flex dynamic light scattering (DLS) instrument (Microtrac Instruments. York PA). Turbidity samples were prepared by placing extruded fluids into 1 cm×1 cm, 3.5 mL polystyrene cuvettes polished on four sides and centrifuging at 2900 relative centrifugal force for 10 minutes to remove air bubbles. Turbidity of the centrifuged samples was measured using a Neulog NUL-231 turbidity sensor and USB-200 interface (products of SES Education, Rishon Lezion, Israel. Turbidity was calculated from the instrument readings using a standard curve prepared from 4000 NTU formazin turbidity standard (catalog number 246142, product of Hach Company, London Ontario) freshly diluted to concentrations between 25 and 800 NTU. For all compositions, concentrations are weight percent.

| patent example | turbidity NTU | hydrophobic drug | hydrophobic therapeutic agent | water immiscible oil |
|---|---|---|---|---|
| 1 COMP | 1100 | | cannabidiol, arnica flower oil | isopropyl myristate, medium chain triglyceride oil, hemp seed oil |
| 2 COMP | 385 | | | |
| 3 COMP | 1150 | ibuprofen | orange essential oil | isopropyl myristate |
| 4 COMP | 402 | lidocaine | | isopropyl myristate, medium chain triglyceride oil, mineral oil |
| 5 INV | 104 | empty | | isopropyl myristate, medium chain triglyceride oil, mineral oil |
| 6 INV | 47 | | tocopherol | isopropyl myristate, medium chain triglyceride oil, mineral oil |
| 7 INV | 104 | lidocaine and benzocaine | | cocoyl caprylocaprate, methyl decanoate, cyclo pentasiloxane, mineral oil |
| 8 INV | 188 | ibuprofen and aspirin | limonene. | isopropyl myristate, soy biodiesel, medium chain triglyceride oil |
| 9 INV | 126 | | cannabidiol, orange essential oil. | isopropyl palmitate, soy biodiesel, hexadecane, medium chain triglyceride oil, cyclo pentasiloxane |
| 10 INV | 66 | | coenzyme Q, retinyl palmitate, ascorbyl palmitate, tocopheryl acetate, cranberry seed oil, black cumin seed oil, raspberry seed oil | isopropyl myristate, medium chain triglyceride oil, isoeicosane, coconut oil, dimethicone, squalane, isohexadecane, isododecane, C23-C15 linear alkane, propylene glycol dicaprylate, sunflower seed oil |
| 11 INV | 212 | | | isopropyl myristate, mineral oil |
| 12 INV | 149 | | tetrahydro cannabinol | isopropyl myristate, mineral oil |
| 13 INV | 97 | | litsea cubeba oil, orange essential oil | medium chain triglyceride oil, isopropyl myristate, ethyl myristate, ethyl oleate, isohexadecane, isododecane, C13-C15 alkane, isoeicosane |
| 14 INV | 363 | | cholecalciferol, birch bark extract, litsea cubeba oil, humulene, myrcene | medium chain triglyceride oil, jojoba oil, isohexadecane, isododecane, |

Example 1 (Comparative)

The particle size and turbidity of a sample of Superior Nano Topical Menthol CBD serum containing 1% cannabidiol, 2% hemp oil, and 1% *Arnica* was measured. The sample has 48.4% lipophilic content, particle diameter=48 nm, number average particle diameter=34 nm and turbidity=1100±200 NTU. Superior Nano Topical Menthol CBD serum is an example of a dense nanolipid fluid (DNLF) dispersion that lacks high transparency.

Example 2 (Comparative)

A mill base was prepared consisting of 9.9% ceteareth-20, 9.9% medium chain triglyceride oil, 9.2 percent isopropyl myristate, 6.6% mineral oil, 5.3% sorbitan oleate, 1.0% soy lecithin, 0.7% BHT, 0.6% phenoxy ethanol, 0.6% tetrasodium EDTA, 0.4% caprylyl glycol, 0.2% citric acid and 55.8% water (total lipid concentration=43.4%). The mill base was prepared by heating all ingredients except for water, sodium EDTA, and citric acid to about 60° C., then adding solution of sodium chloride plus sodium EDTA plus citric acid while mixing with an overhead stirrer to give a viscous, opaque dispersion. The mill base volume average diameter was about 1270 nm and number average diameter was about 171 nm.

The mill base was processed using a Leistritz 27 mm twin screw extruder which had been modified by removing the cooling water manifold and the hoses between the manifold and the barrel and replacing with ½ inch ID braided flexible clear PVC tubing that connected the motor end entrance of each barrel section cooling channel to the die end entrance of the cooling channel of the preceding (closer to the motor) section of the extruder barrel. Chilled propylene glycol/water coolant was supplied to the extruder barrel at between 0.1 and 1.2° C. with a recirculating chiller in a counter flow orientation (that is, entering the extruder barrel at the die end and exiting the extruder barrel at the motor end). Mill base was provided to the extruder entrance using a gear pump after flowing through the inner channel of a stainless steel counter flow wort chiller with water at 95° C. flowing in a counter flow direction through the outer channel. The screw configuration of the extruder included alternating sections of 30 mm and 40 mm pitch intermeshing screw elements. The temperature of the mill base entering the extruder was about 90° C., the extruded mill base temperature was about 15° C., and the screw rotation rate was 200 rpm.

The extruded product had the appearance of a light brown translucent liquid with viscosity of corn syrup. The volume average particle diameter was 48 nm and the number average particle diameter was about 34 nm when measured by DLS (Dynamic Light Scattering) and the turbidity was 385±20 NTU. The extruded mill base is an example of a DNLF dispersion that lacks high transparency.

Example 3 (Comparative)

A mill base was prepared consisting of 3.0% sorbitan oleate (Making Cosmetics, Redmond, WA), 0.5% dioleyl phosphatidyl choline (Phospholipon 90G, product of Lipoid USA, Newark, NJ), 1.1% of capric/caprylic triglyceride oil (Lotioncrafter, Eastsound, WA), 6.1% laureth-23 (Lotioncrafter, Eastsound, WA), 4.6% PEG 100 stearate (Myrj S100, available from Spectrum Chemical), 20.2% isopropyl myristate (Lotioncrafter, Eastsound, WA), 5.1% ibuprofen (BASF, Florham Park, NJ), 5.1% of cold pressed orange oil (Blue Water Chem Group, Fort Wayne IN), 0.5% Optiphen preservative (Lotioncrafter, Eastsound, WA), 0.1% tetrasodium EDTA (Making Cosmetics, Redmond, WA), 0.03% anhydrous citric acid and 53.7% water was prepared by mixing and heating all ingredients but water, EDTA and citric acid to 60° C. and then adding these three ingredients as a solution while mixing with an overhead stirrer, giving a viscous, slightly translucent opaque ivory colored liquid. The mill base was processed as described in Example 2 to give a viscous bluish translucent ivory colored liquid with volume average diameter equal 60 nm and number average diameter 38 nm. The sample turbidity was 1150±200 NTU when measured using the Neulog turbidity meter. The extruded mill base is an example of a DNLF dispersion that lacks high transparency.

Example 4 (Comparative)

A lipid nanoparticle dispersion was made and processed as described in Example 54 of U.S. patent application Ser. No. 16/748,399 with 35.1 weight lipophilic phase concentration containing 6.9% ceteareth-20, 1.8% lidocaine, 7.0% sorbitan stearate, 7.0% isopropyl myristate, 6.0% capric/caprylic triglyceride, oil, 6.5% light mineral oil, 0.02% NaCl, and 64.8 weight percent (%) water. The sample had volume average particle diameter=28 nm and turbidity=400 NTU. The extruded mill base is an example of a DNLF dispersion that lacks high transparency.

Example 5 (Inventive)

A mill base was prepared that contained 13.4% ceteareth-20, 5.5% mineral oil, 8.5% medium chain triglyceride oil, 8.6% isopropyl myristate, 1.2% Jeecide CAP-4 preservative, 10.1% sorbitan oleate, and 52.7% water. The lipophilic content of the mill base was 46.1% and the sum of the concentration of water insoluble oil plus hydrophobic therapeutic agent was 22.6%. The polyethoxylated high HLB surfactant content was 13.4%, the low HLB surfactant content was 10.1%, and the aqueous phase content was 52.7%. The mill base formed a clear microemulsion when heated above 50° C. The mill base was processed as described in Example 2, giving a clear water white gel DNLF dispersion product. The sample had volume average particle diameter=27 nm and turbidity=104. The extruded mill base is an example of a highly transparent lipid nanoparticle dispersion with lipophilic content greater than 25% without active ingredients.

Example 6 (Inventive)

A mill base was prepared that contained 6.7% ceteareth-20, 2.0% laureth-23, 4.7% ceteareth-30, 7.8% sorbitan oleate, 2.0% Alcolec XTRA-A soy lecithin, 9.2% mineral oil, 7.5% medium chain triglyceride oil, 7.5% isopropyl myristate, 0.8% tocopherol, 1.3% Jeecide CAP-4 preservative, 0.4% sodium phytate, 0.2% citric acid, 7.6% glycerin and 42.2% water. The lipophilic content of the mill base was 48.2% and the sum of the concentration of water insoluble oil plus hydrophobic therapeutic agent was 25.0%. The polyethoxylated high HLB surfactant content was 13.4%, the low HLB surfactant content was 9.8%, and the aqueous phase content was 50.4%. The mill base formed a clear microemulsion when heated above 50° C. The mill base was processed as described in Example 2, giving a clear yellow soft gel product. The sample had volume average particle diameter=37 nm and turbidity=47 NTU. The extruded mill base is an example of a highly transparent lipid nanoparticle dispersion with tocopherol, a hydrophobic therapeutic agent and with lipophilic content greater than 25%.

Example 7 (Inventive)

A mill base was prepared that contained 9.2% Lotionpro 165 (emulsifier blend which includes glyceryl stearate and polyoxyethylene stearate (PEG-100 stearate), Lotioncrafter), 2.1% polysorbate 80 (Lotioncrafter), 7.2% ceteareth-20, 0.8% sorbitan oleate, 1.6% Alcolec XTRA-A soy lecithin, 5.4% caproyl caprylocaprate (BASF Kollicream 3C), 7.2% methyl decanoate (CE-1095 from Proctor and Gamble), 7.2% cyclopentasiloxane (Lotioncrafter), 2.7% mineral oil (Drakeol 7 from CQ concepts), 2.1% lidocaine, 1.8% benzocaine, 1.1% Jeecide CAP-4 preservative, 8.3% glycerin and 43.3% water. The lipophilic content of the mill base was 47.3% and the sum of the concentration of water insoluble oil plus hydrophobic therapeutic agent was 26.4%. The aqueous phase content was 51.6%. The mill base was processed as described in Example 2, giving a clear yellow soft gel product. The sample had volume average particle diameter=23.6 nm and turbidity=105 NTU. After 100 days at room temperature, the volume average particle size increased to 264 nm and the increase in particle size shows that the DNLF fluid is not at equilibrium, that is, it is a non-equilibrium system. The extruded mill base is an example of a highly transparent lipid nanoparticle dispersion comprising lidocaine and benzocaine, two hydrophobic drugs with lipophilic content greater than 25%.

Example 8 (Inventive)

A mill base was prepared that contained 9.6% Lotionpro 165, 0.8% steareth-40 (Ethox), 7.1% ceteareth-30, 0.8% sorbitan oleate, 2.0% Alcolec XTRA-A soy lecithin, 6.0% isopropyl myristate, 8.0% medium chain triglyceride oil, 2.0% soy biodiesel, 6.7% limonene, 2.0% cold pressed orange oil, 2.0% ibuprofen, 0.9% aspirin, 1.2% Jeecide CAP-4 preservative, 0.6% tetrasodium EDTA, 0.2% citric acid, 2.0% diethylene glycol monoethyl ether (Transcutol, product of Gattefosse), 6.0% glycerin and 41.8% water. The lipophilic content of the mill base was 47.9% and the sum of the concentration of water insoluble oil plus hydrophobic therapeutic agent was 27.6%. The aqueous phase content was 49.8%. The mill base was processed as described in Example 2, giving a clear yellow soft gel product. The sample had volume average particle diameter=49 nm and turbidity=188 NTU. A sample of extruded product (19 g) was placed in a 30 mL beaker and carefully warmed with a torch until the viscosity dropped so as to be stirred with a magnetic stirrer, about 50° C., and the beaker was placed on a hot plate stirrer and heated slowly while observing between two crossed polarizing films. The sample was transparent and birefringent in the temperature range between 62 and 66° C., indicating that it possessed latent lamellar structure. After 100 days at room temperature, the volume average particle size increased to 351 nm and the increase in particle size shows that the DNLF fluid is not at equilibrium, that is, it is a non-equilibrium system. The extruded mill base is an example of a highly transparent lipid nanoparticle dispersion with lipophilic content greater than 25% that comprises hydrophobic drugs (ibuprofen and acetyl salicylic acid) and a hydrophobic therapeutic agent (limonene) that is a non-equilibrium system and has a latent lamellar structure.

Example 9 (Inventive)

A mill base was prepared that contained 11.0% Gelot 64 (mixture of glycerol monostearate and PEG-75 stearate, Gattefosse), 3.7% laureth-23 (Ethox), 5.8% ceteareth-20, 3.3% isopropyl palmitate, 6.6% medium chain triglyceride oil, 3.3% soy biodiesel (MN Soy Processors), 1.1% hexadecane, 2.9% cold pressed orange oil, 2.9% cyclopentasiloxane, 1.0% cannabidiol, 1.0% Jeecide CAP-4 preservative, 9.8% glycerin and 47.7% water. The lipophilic content of the mill base was 41.6% and the sum of the concentration of water insoluble oil plus hydrophobic therapeutic agent was 21.1%. The aqueous phase content was 57.5%. The mill base was processed as described in in Example 2, giving a clear yellow soft gel product. The sample had volume average particle diameter=39 nm and turbidity=126 NTU. The extruded mill base is an example of a highly transparent lipid nanoparticle dispersion with lipophilic content greater than 25% that comprises cannabidiol, a hydrophobic cannabinoid compound. After 100 days at room temperature, the volume average particle size increased to 1357 nm and the increase in particle size shows that the DNLF fluid is not at equilibrium, that is, it is a non-equilibrium system.

Example 10 (Inventive)

A mill base was prepared that contained 7.4% Lotionpro 165, 1.3% Lipomulse 165 (emulsifier blend which includes glyceryl stearate and polyoxyethylene stearate (PEG-100 stearate), Lipo Chemicals), 4.1% ceteareth-20, 1.7% ceteareth-30, 0.9% laureth-23, 3.2% oleic acid, 1.1% propylene glycol dicaprylate, 0.9% coconut oil, 8.6% isopropyl myristate, 2.0% DM6 dimethicone (Lotioncrafter), 1.9% squalane (Lotioncrafter), 1.9% Siclone SR-5 (Presperse, Somerset NJ), 1.9% isoeicosane (MakingCosmetics), 2.2% Renew oil (product of Botanic Innovations, Spooner WI), 1.9% tocopheryl acetate (Lotioncrafter), 0.3% coenzyme Q (Lotioncrafter), 2.1% ascorbyl palmitate (MakingCosmetics), 0.5% retinyl palmitate (MakingCosmetics), 1.0% Jeecide CAP-4 preservative, 0.6% tetrasodium EDTA, 0.2% citric acid, 7.8% glycerin and 46.2% water. The lipophilic content of the mill base was 43.9% and the sum of the concentration of water insoluble oil plus hydrophobic therapeutic agent was 25.3%. The aqueous phase content was 54.8%. The mill base was processed as described Example 2, giving a clear yellow soft gel product. The sample had volume average particle diameter equal to 40 nm and turbidity=66 NTU. After 100 days at room temperature, the volume average particle size increased to 578 nm and the increase in particle size shows that the DNLF fluid is not at equilibrium, that is, it is a non-equilibrium system. A sample (100 g) of the extruded product was placed in a 150 mL beaker and carefully warmed to 50° C. to reduce the viscosity so as to allow stirring with a magnetic stirrer. The warmed, stirring sample was heated further using the stirrer hotplate while observing between crossed polarizing films. It was found to be transparent and birefringent in the temperature range of 70 to 72° C., indicating that it has latent lamellar structure. The extruded mill base is an example of a non-equilibrium highly transparent lipid nanoparticle dispersion with latent lamellar structure and lipophilic content greater than 25% that includes hydrophobic therapeutic agents retinyl palmitate, ascorbyl palmitate, tocopherol, coenzyme Q, cranberry seed oil, raspberry seed oil, and black cumin seed oil.

Example 11 (Inventive)

A mill base was prepared that contained 12.1% polysorbate 80, 2.4% polysorbate 20, 1.0% sodium stearoyl lactylate, 4.0% sorbitan oleate, 1.5% soy lecithin, 2.0% stearic acid, 26.7% isopropyl myristate, 10.9% light mineral oil, 2.0% niacinamide, 0.1% citric acid, 6.0% glycerin, and 31.2% water. The lipophilic content of the mill base was 60.6% and the sum of the concentration of water insoluble oil plus hydrophobic therapeutic agent was 37.6%. The polyethoxylated high HLB surfactant content was 14.5%, the low HLB surfactant content was 7.5%, and the aqueous phase content was 39.3%. When heated to above 50° C., the mill base formed a clear microemulsion. The mill base was processed as described in in Example 2 to give a lipid nanoparticle dispersion as a clear yellow soft gel product. When diluted with water and analyzed by DLS, the lipid nanoparticle dispersion was observed to have volume average particle diameter equal to 58 nm. The sample turbidity was 212 NTU. The lipid nanoparticle dispersion is an example of an edible highly transparent DNLF dispersion in which all of the components are listed on the US Food and Drug Administration Inert Ingredient Guide (IIG) and/or approved for direct addition to food for humans (21CFR Part 172). What this example shows is that a mill base can be processed using a twin screw extruder to give an edible highly transparent, highly concentrated non-equilibrium DNLF dispersion with lipophilic content greater than 25%.

Example 12 (Inventive)

A mill base was prepared that contained 12.0% polysorbate 80, 2.4% polysorbate 20, 1.0% sodium stearoyl lactylate, 4.0% sorbitan oleate, 1.5% soy lecithin, 2.0% stearic acid, 26.4% isopropyl myristate, 10.8% light mineral oil, 1.1% delta-8 tetrahydrocannabinol, 2.0% niacinamide, 0.1% citric acid, 6.0% glycerin, and 30.9% water. The lipophilic content of the mill base was 61.21% and the sum of the concentration of water insoluble oil plus hydrophobic therapeutic agent was 38.3%. The polyethoxylated high HLB surfactant content was 14.4%, the low HLB surfactant content was 7.5%, and the aqueous phase content was 39.0%. The mill base was processed as described in in Example 2 except the mill base was heated batch wise to 95° C. and poured manually into the extruder inlet to give a clear yellow soft gel DNLF dispersion product. When diluted with water and analyzed by DLS, the DNLF dispersion was observed to have volume average particle diameter equal to 58 nm. The sample turbidity was 149 NTU. The DNLF dispersion was administered to a human subject by placing in the sublingual and buccal compartments of the mouth (sublingual and buccal administration, respectively). The DNLF dispersion (400 mg) was placed into a gelatin capsule and administered to a human subject by swallowing (oral administration). The extruded DNLF dispersion is an example of an edible highly transparent lipid nanoparticle dispersion in which all of the components are listed on the US Food and Drug Administration Inert Ingredient Guide (IIG) and/or approved for direct addition to food for humans (21CFR Part 172). What this example shows is that a mill base can be processed using a twin screw extruder to give an edible highly transparent, aqueous dispersion of lipid nanoparticles with lipophilic content greater than 25% comprising tetrahydrocannabinol, a hydrophobic therapeutic agent.

Example 13 (Inventive)

A mill base was prepared that contained 10.1% ceteareth-20, 1.6% Cremophor RH40 (product of BASF), 2.2% Kolliphor HS15 (product of BASF), 1.5% glyceryl oleate, 0.5% Maisine CC (glyceryl monolinoleate, product of Gattefosse), 8.0% sorbitan stearate, 8.3% medium chain triglyceride oil, 2.3% isopropyl myristate, 1.0% ethyl myristate, 3.0% ethyl oleate, 6.0% Siclone SR-5, 0.3% *Litsea cubeba* oil, 0.1% concentrated orange essential oil, 1.1% Jeecide CAP-4, 1.8% urea, 0.2% NaCl, and 52.0% water. The lipophilic content of the mill base was 44.9% and the sum of the concentration of water insoluble oil plus hydrophobic therapeutic agent was 21.0%. The polyethoxylated high HLB surfactant content was 13.9%, the low HLB surfactant content was 10.0%, and the aqueous phase content was 54.0%. The mill base was prepared by heating all ingredients except for urea, NaCl and water to 70° C. and adding a room temperature solution of urea and NaCl in water while stirring with an overhead stirrer. The mill base was processed as described in in Example 2 except the mill base was heated batch wise to 93° C. and poured manually into the extruder inlet. The extruded DNLF dispersion product was a clear white viscous liquid. When diluted with water and analyzed by DLS, the sample was observed to have volume average particle diameter equal to 35.5 nm. The sample turbidity was 97 NTU. A 39 gram sample of the DNLF dispersion was placed in a 50 mL beaker and carefully heated for 2 second intervals using a 700 W microwave oven on defrost setting with stirring in between intervals to gradually and evenly raise the temperature to about 40° C., enabling the sample to be stirred with a magnetic stirrer/hotplate. The sample was heated and stirred using the hotplate up to about 80° C. while recording temperature and conductivity and observing for birefringence. It was not birefringent below about 60° C. and was observed to be birefringent between 6° and 62° C. and again at 75° C., indicating that the DNLF dispersion has latent lamellar structure. The plot of conductivity vs temperature showed a negative peak with negative peak maximum amplitude (local minimum) at 72° C. and a positive peak in the plot of d(normalized conductivity)/dT vs temperature at 75° C. with peak amplitude 0.6° C.$^{-1}$ which is additional evidence that the DNLF dispersion has latent lamellar structure. After standing at between 2° and 25° C. for one week, the unprocessed mill base was an opaque liquid, indicating that the transparent extruded DNLF dispersion product is a non-equilibrium lipid nanoparticle dispersion. This example shows that a composition containing surfactants ceteareth-20, PEG40 hydrogenated castor oil, PEG15 hydroxy stearate, glyceryl oleate, glyceryl monolinoleate and sorbitan stearate plus oils including medium chain triglyceride oil, isopropyl myristate, ethyl oleate, ethyl myristate, isodohexadecane, isododecane, C10-C13 alkane and hydrophobic therapeutic agents *Litsea cubeba* oil and orange essential oil can be processed using a twin screw extruder to give a non-equilibrium lipid nanoparticle dispersion with lipophilic content greater than 25% and less than 100 NTU turbidity and latent lamellar structure.

Example 14 (Inventive)

A mill base was prepared that contained 3.9% Emulcire 61 WL 2659 (product of BASF), 2.0% ceteareth-20, 2.3% ceteareth-20, 3.7% laureth-23, 1.4% sodium lauryl sulfate, 3.3% Alcolec XTRA-A soy lecithin, 2.6% stearic acid, 3.9% Gelucire 50/13 (PEG32 stearate, product of BASF), 5.4% medium chain triglyceride oil, 4.2% isopropyl myristate, 1.7% jojoba oil, 4.5% isohexadecane, 2.4% isododecane, 1.2% of a 1000 IU vitamin D3 (cholecalciferol) solution in medium chain triglyceride oil, 0.2% birch bark extract, 0.3% *Litsea cubeba* oil, 0.7% Jeecide CAP-4, 0.8% humulene, 1.4% myrcene, 0.5% caffeine, 0.2% super low molecular weight hyaluronic acid (product of Making Cosmetics), 0.5% niacinamide, 0.5% alpha arbutin, 0.5% kojic acid, 0.4% sodium phytate, 0.5% sodium benzoate, 0.1% citric acid, 7.2% glycerin, and 43.6% water. The lipophilic content of the mill base was 45.2% and the sum of the concentration of water insoluble oil plus hydrophobic therapeutic agent was 22.1%. The aqueous phase content was 44.3%. The mill base was processed as described in in Example 2 except the mill base was heated batch wise to 98° C. and poured manually into the extruder inlet, giving a clear orange gel DNLF dispersion product. When diluted with water and analyzed by DLS, the sample was observed to have volume average particle diameter equal to 47.2 nm. The DNLF dispersion was administered to a human subject by applying 400 mg to a knee with skin area approximately 100 cm$^2$ (cutaneous administration). The sample was placed in a 1 cm path length polystyrene cuvette and air bubbles were removed by centrifuging at 2900 relative centrifugal force for 40 minutes at 18° C. The sample turbidity was 365 NTU. After standing at between 20 and 25° C. for one week, the mill base was an opaque liquid, indicating that the transparent extruded product is a non-equilibrium DNLF. What this example shows is that a composition comprising birch bark extract, jojoba oil, cholecalciferol, *Litsea cubeba* oil, humulene, myrcene, caffeine, niacinamide, alpha arbutin, kojic acid and hyaluronic acid in a base of surfactants including ceteareth-20, ceteareth-30, Emulcire EM61 WL, Gelucire 50/13, laureth-23, lecithin and stearic acid plus oils including jojoba oil, medium chain triglyceride oil, isopropyl myristate, isododecane, and isohexadecane can be processed using a twin screw extruder to give a non-equilibrium lipid nanoparticle dispersion with lipophilic content greater than 25% and turbidity less than 375 NTU.

The invention claimed is:
1. A lipid nanoparticle dispersion comprising:
   from 11.1 to 19.8 wt. % of one or more polyethoxylated high hydrophile-lipophile-balance (HLB) surfactants selected from the group consisting of laureth-23, ceteareth-20, ceteareth-30, steareth-40, PEG32 stearate, PEG75 stearate, PEG100 stearate, PEG15 hydroxy stearate, PEG40 hydrogenated castor oil, polysorbate 20, polysorbate 80, and combinations thereof;
   from 3.3 to about 10.1 wt. % of one or more low hydrophile-lipophile-balance (HLB) surfactants selected from the group consisting of cetyl alcohol, glyceryl oleate, glyceryl stearate, glyceryl monolinoleate, oleic acid, stearic acid, sorbitan oleate, soy lecithin, and combinations thereof;
   one or more water immiscible oils selected from the group consisting of medium chain triglyceride oil, coconut oil, isopropyl palmitate, isopropyl myristate, methyl decanoate, ethyl myristate, ethyl oleate, mineral oil, orange essential oil, cyclopentasiloxane, poly(dimethyl siloxane), hexadecane, propylene glycol dicaprylate, isododecane, isoeicosane, isohexadecane, soy biodiesel, jojoba oil, cocoyl caprylocaprate, $C_{10}$-$C_{13}$ alkane, squalane, sunflower seed oil, and combinations thereof; and water,
wherein the lipid nanoparticle dispersion has a lipophilic concentration greater than about 25%, a volume average particle size less than about 100 nm, and a turbidity less than 375 nephelometric turbidity units (NTU) at room temperature.

2. The lipid nanoparticle dispersion of claim 1, further comprising one or more hydrophobic drugs selected from the group consisting of aspirin, benzocaine, ibuprofen, lidocaine, and combinations thereof.

3. The lipid nanoparticle dispersion of claim 1 further comprising one or more hydrophobic therapeutic agents selected from the group consisting of ascorbyl palmitate, birch bark extract, cannabidiol, ubiquinone, cholecalciferol, tetrahydrocannabinol, humulene, myrcene, *Litsea cubeba* oil, limonene, cranberry seed oil, raspberry seed oil, black cumin seed oil, retinyl palmitate, tocopheryl acetate, tocopherol, and combinations thereof.

4. The lipid nanoparticle dispersion of claim 1 having a latent lamellar structure.

5. The lipid nanoparticle dispersion of claim 1 that is a non-equilibrium lipid nanoparticle dispersion.

6. The lipid nanoparticle dispersion of claim 1, wherein a concentration of water immiscible non-amphipathic compounds is greater than about 20%.

7. The lipid nanoparticle dispersion of claim 1, further comprising a non-ethoxylated high hydrophile-lipophile-balance (HLB) surfactant selected from the group consisting of sodium lauryl sulfate, sodium stearoyl lactylate, and combinations thereof.

8. The lipid nanoparticle dispersion of claim 1 having a turbidity less than 250 nephelometric turbidity units (NTU) at room temperature.

9. The lipid nanoparticle dispersion of claim 1 having a turbidity less than 125 nephelometric turbidity units (NTU) at room temperature.

10. The lipid nanoparticle dispersion of claim 1 that does not include one or more co-solvents.

11. The lipid nanoparticle dispersion of claim 1 that does not include ibuprofen.

12. The lipid nanoparticle dispersion of claim 1 that does not include lidocaine.

13. The lipid nanoparticle dispersion of claim 1 wherein the lipid nanoparticles are not vesicular nanoparticles.

14. The lipid nanoparticle dispersion of claim 1 having a latent lamellar structure wherein the lipid nanoparticles are not vesicular nanoparticles.

15. The lipid nanoparticle dispersion of claim 1 having a volume average particle diameter in a range from 23.6 nm to 58 nm.

16. The lipid nanoparticle dispersion of claim 1, further comprising a cryoprotectant.

17. The lipid nanoparticle dispersion of claim 16, wherein the cryoprotectant comprises 6 to 9.8 wt. % glycerin.

18. The lipid nanoparticle dispersion of claim 1, comprising more than one high HLB surfactant.

19. The lipid nanoparticle dispersion of claim 1, wherein the one or more water immiscible oils comprises cyclopentasiloxane.

20. The lipid nanoparticle dispersion of claim 1, wherein the one or more water immiscible oils comprises mineral oil.

21. The lipid nanoparticle dispersion of claim 3, wherein the one or more hydrophobic therapeutic agents comprises limonene.

22. The lipid nanoparticle dispersion of claim 1 having a turbidity in a range from 47 to 365 nephelometric turbidity units (NTU) at room temperature.

23. A lipid nanoparticle dispersion comprising:
from about 10 to about 15 wt. % of one or more polyethoxylated high hydrophile-lipophile-balance (HLB) surfactants selected from the group consisting of laureth-23, ceteareth-20, ceteareth-30, steareth-40, PEG32 stearate, PEG75 stearate, PEG100 stearate, PEG15 hydroxy stearate, PEG40 hydrogenated castor oil, polysorbate 20, polysorbate 80, and combinations thereof;
from about 8 to about 12 wt. % of one or more low hydrophile-lipophile-balance (HLB) surfactants selected from the group consisting of cetyl alcohol, glyceryl oleate, glyceryl stearate, glyceryl monolinoleate, oleic acid, stearic acid, sorbitan oleate, soy lecithin, and combinations thereof;
from about 20 to about 40 wt. % of one or more water immiscible oils selected from the group consisting of medium chain triglyceride oil, coconut oil, isopropyl palmitate, isopropyl myristate, methyl decanoate, ethyl myristate, ethyl oleate, mineral oil, orange essential oil, cyclopentasiloxane, poly(dimethyl siloxane), hexadecane, propylene glycol dicaprylate, isododecane, isoeicosane, isohexadecane, soy biodiesel, jojoba oil, cocoyl caprylocaprate, $C_{10}$-$C_{13}$ alkane, squalane, sunflower seed oil, and combinations thereof; and
from about 35 to about 60 wt. % water,
wherein the lipid nanoparticle dispersion has:
a lipophilic concentration greater than about 25%;
a volume average particle size less than about 100 nm; and
a turbidity less than 375 nephelometric turbidity units (NTU).

* * * * *